(12) United States Patent
Cacioppo et al.

(10) Patent No.: US 7,214,187 B2
(45) Date of Patent: May 8, 2007

(54) SYSTEM AND METHOD FOR IDENTIFICATION OF FALSE STATEMENTS

(75) Inventors: John T. Cacioppo, Flossmoor, IL (US); Tyler S. Lorig, Fairfield, VA (US)

(73) Assignee: The University of Chicago, Chicago, IL (US)

( * ) Notice: Subject to any disclaimer, the term of this patent is extended or adjusted under 35 U.S.C. 154(b) by 49 days.

(21) Appl. No.: 10/499,070

(22) PCT Filed: Dec. 18, 2002

(86) PCT No.: PCT/US02/40436

§ 371 (c)(1),
(2), (4) Date: Nov. 10, 2004

(87) PCT Pub. No.: WO03/059161

PCT Pub. Date: Jul. 24, 2003

(65) Prior Publication Data

US 2005/0065413 A1    Mar. 24, 2005

(51) Int. Cl.
*A61B 5/00* (2006.01)
(52) U.S. Cl. .............. 600/300; 600/301; 600/587; 128/903; 128/904; 128/905
(58) Field of Classification Search ........ 600/300–301, 600/587; 128/903–905
See application file for complete search history.

(56) References Cited

U.S. PATENT DOCUMENTS 5,588,425 A    12/1996    Sackner et al.
5,771,261 A    6/1998    Anbar
5,853,005 A    12/1998    Scanlon
6,322,515 B1    11/2001    Goor et al.

FOREIGN PATENT DOCUMENTS

WO    WO 03/05161 A1    7/2003

OTHER PUBLICATIONS

Oberlin, M., Verbal Conditioning of the Galvanic Skin Responses to Deception, Department of Defense—Polygraph Institute Research Division, Report No. DoDPI94-R0018, Jun. 1994.*
Chaves, Jose, MD, Biofeedback: the therapy of the 21st Century, Brain & Mind, No. 4, Dec. 1997-Feb. 1998.*
Int'l. Search Report Jun. 16, 2003.

* cited by examiner

*Primary Examiner*—Max F. Hindenburg
*Assistant Examiner*—Filip A. Kowalewski
(74) *Attorney, Agent, or Firm*—Barnes & Thornburg LLP; Alice O. Martin

(57) ABSTRACT

A method of detecting lie detection including the steps of first conditioning the subject to produce an involuntary physiological response triggered when the subject provides false statements; and secondly asking the subject to state whether each of series of statements presented to the subject are true. As the subject answers, the subject is monitored for the conditioned involuntary response. Detecting whether the subject is providing false statements is based on whether the involuntary response is observed during these answers. A system (19) for lie detection includes a computing device (21), a controller (40), and at least one conditioning interface (42, 44).

19 Claims, 6 Drawing Sheets

SYSTEM AND METHOD FOR IDENTIFICATION OF FALSE STATEMENTS

BACKGROUND

The present invention relates to a system and method of detecting when a subject is lying by conditioning the subject to produce a unique physiological response which is not a naturally occurring physiological phenomenon, in contrast to the prior methods which rely on monitoring natural responses. Specifically, using classical Pavlovian conditioning techniques and semantic generalization, a unique autonomic response is created in test subjects when they are exposed to a true versus a false statement (conditioned stimuli). This assures that an independent assessment can be made of whether a given examinee shows the conditioned response to known questions and allows quantitative comparisons of conditioned responses to the critical questions to be compared to the distribution of conditioned responses shown to known true and known false statements.

Current lie detection methods, based on the polygraph technique, rely upon detecting changes in the physiological characteristics of the subject. Among the characteristics measured are respiration rate, skin resistivity, blood pressure, and heart rate. One such method is the relevant/irrelevant test (RIT). As the name implies, the subject is asked a series of relevant and irrelevant questions. Measurements of the subject's physiological characteristics are made while the subject is answering these questions. If the physiological response to the relevant questions is greater than to the irrelevant questions, the subject is deemed to be deceptive. Responses of equivalent size to the two types of questions indicate truthfulness.

Another approach is the control question test (CQT). The CQT involves a comparison of responses to relevant questions, to certain control questions which are designed to elicit emotional reactions (e.g. "Have you ever taken something from someone who trusted you?"). Assuming that everyone has done the sorts of things asked in the control questions, innocent people should react more strongly to control questions than relevant questions. Conversely, dishonest people should react more strongly to relevant questions than control questions.

Yet another method is the Guilty Knowledge Test (GKT). In the GKT the subject is asked a series of multiple choice questions, all dealing with facts with which only those knowledgeable about the crime would be familiar. The GKT assumes that the guilty individual's recognition of the correct multiple choice alternative that contains actual details of the crime will lead to stronger physiological responses than to incorrect alternatives.

The technology used to monitor and record physiological measurements used by the polygrapher is typically a portable field polygraph. Recorded activity includes electrodermal responsivity (for example skin resistance or conductance), monitored from stainless steel electrodes attached to the fingertips; respiration, recorded from pneumatic belts positioned around the upper chest and abdomen; and a "cardio" channel in which relative changes in blood pressure are determined by observing pressure oscillations obtained from a standard, partially inflated sphygmomanometer cuff placed on the subjects arm. Some methods may also record brain activity using electro-encephalography to measure P3 brain waves. Records are made either mechanically or are digitized and stored in a computer.

Even with control questions, the problem with all three of the methods described in previous paragraphs is that they rely on monitoring natural physiological responses which may fluctuate for reasons other than deceptive conduct or response to questions by the subject. Other potential problems and limitations are outlined in the National Research Council (2002) report on the scientific validity of the polygraph. Predictably, these methods produce false negatives (i.e. a deception is missed) and false alarms (subject is not lying, but inquisitor believes subject is). The problem of false positives and false negatives would be lessened if a novel autonomic pattern were semantically conditioned to true statements and the opposite novel autonomic pattern were semantically conditioned to false statements. These autonomic patterns would be involuntary, innocuous, and visibly undetectable, yet more accurate (i.e. lower false alarm rate) and sensitive (i.e. low false negative rate) than the traditional approaches described above.

Another problem with these traditional approaches is that they may be vulnerable to the deployment of countermeasures by the subject (National Research Council, 2002). Subjects who are aware that showing a stronger physiological response to control questions than to relevant questions is indicative of truthfulness can manipulate their physiology using cognitive, emotional, or motoric acts to influence their physiological responses to questions. One known countermeasure is increasing breathing by methods such as holding one's breath for 5–20 seconds after answering a control question. Another known countermeasure is to increase one's heart rate using methods such as constricting one's anal sphincter muscle, biting down on the tongue, or thinking exciting thoughts. Because of the effectiveness of such countermeasures, there is a need for a detectable response to lying that are more difficult to manipulate by the subject during testing.

SUMMARY OF THE INVENTION

The present invention relates to a system and method of detecting when a subject is lying by conditioning the subject to produce a unique physiological response which is not a naturally occurring physiological phenomenon, in contrast to the prior methods which rely on monitoring natural responses. Specifically, using classical Pavlovian conditioning techniques and semantic generalization, a unique autonomic response is created in test subjects when they are exposed to a true versus a false statement (conditioned stimuli). This assures that an independent assessment can be made of whether a given examinee shows the conditioned response to known questions and allow quantitative comparison of conditioned responses to the critical questions to be compared to the distribution of conditioned responses shown to known true and known false statements.

One embodiment of the conditioned physiological response is vasomotor activity—an innocuous and reflexive response to mild heating and cooling of the skin. Because of the way conditioning is accomplished (one site is conditioned to show vasoconstriction and another is conditioned to show vasodilation to a true statement, vice versa when presented with false statements), the reflexive response pattern is not observable naturally. That is, there is a near zero baserate for this pattern of response.

Disclosed is a system and the system's method of use which maybe described as generally involving three stages. First, semantic conditioning is used to produce a bidirectional vasomotor/physiological response that otherwise would not occur (zero baserate). Second, a conditioning and testing procedure is implemented based on semantic generalization. Third, data from this second stage is used to assess the truth or falsehood of intermittent test statements based on an observed pattern of conditioned responses. The entire conditioning, testing, and assessment procedure may be fully automated, thereby standardizing testing and avoiding confounding influences of examiner expectations or examiner/examinee interactions or rapport.

The differential conditioning used to form novel and distinctive patterns of physiological response makes it difficult for countermeasures to be used by the subject that are not detected during the presentation of known control questions in the second phase of the study. Moreover, the conditioned response is not visible to the naked eye. This is advantageous over a visible response such as training the subject to blink, which would result in the subject blinking to falsehoods after leaving the examination environment. In contrast, vasoconstriction or vasodilation is not obvious.

An aspect of this invention is a system for detecting false statements made by a subject which includes a programmed computing device, an output device configured to receive data from the programmed computing device. Also included is a controller configured to be operated by the programmed computing device which controls at least one conditioning interface. Each conditioning interface includes a physiological measuring device and an attachment structure for attaching the conditioning device to a selected body part of a test subject.

Also disclosed is a method of using the above system. This method of use includes first attaching the conditioning interfaces to the subject. Next, the subject is conditioned to produce an involuntary physiological response when the subject states a false statement. Further, the method includes subjecting the subject to a testing stage which involves presenting the subject with a series of questions and recording the subject's answers to the series of questions while contemporaneously recording data related to the involuntary physiological response. After the data is collected, it is analyzed to determine whether the subject is providing false statements.

The step of conditioning the subject to produce an involuntary physiological response described above involves: (a) exposing the subject to a statement that is true statement to the subject; (b) stimulating a first body part of the subject with a first stimulus and contemporaneously stimulating a second body part of the subject with a second stimulus to obtain a first conditioned physiological response which is designated the true response; and (c) repeating a cycle of steps a–b.

For the method described above, exposing the subject to a statement may be displaying the statement on a screen. In the alternative, exposing the subject to a statement may be by producing the statement audibly for the subject to hear.

Also for the method described above, the physiological response is a vasoconstriction of blood vessels in the first body part, and vasodilation of the blood vessels in the second body part. In the alternative, the physiological response may be a blinking of an eye. Further, for the method described above, the first stimulus and second stimulus may be only applied during a subset of the cycle.

Finally, the invention includes a method of detecting lie detection. First, the subject is conditioned to produce an involuntary physiological response triggered when the subject provides false statements. Next, the subject is asked to state whether each of a series of statements presented to the subject are true. As the subject answers, the subject is monitored for the conditioned involuntary response. Detecting whether the subject is providing false statements is based on whether the involuntary response is observed during these answers.

DETAILED DESCRIPTION OF THE INVENTION

Figure 1:
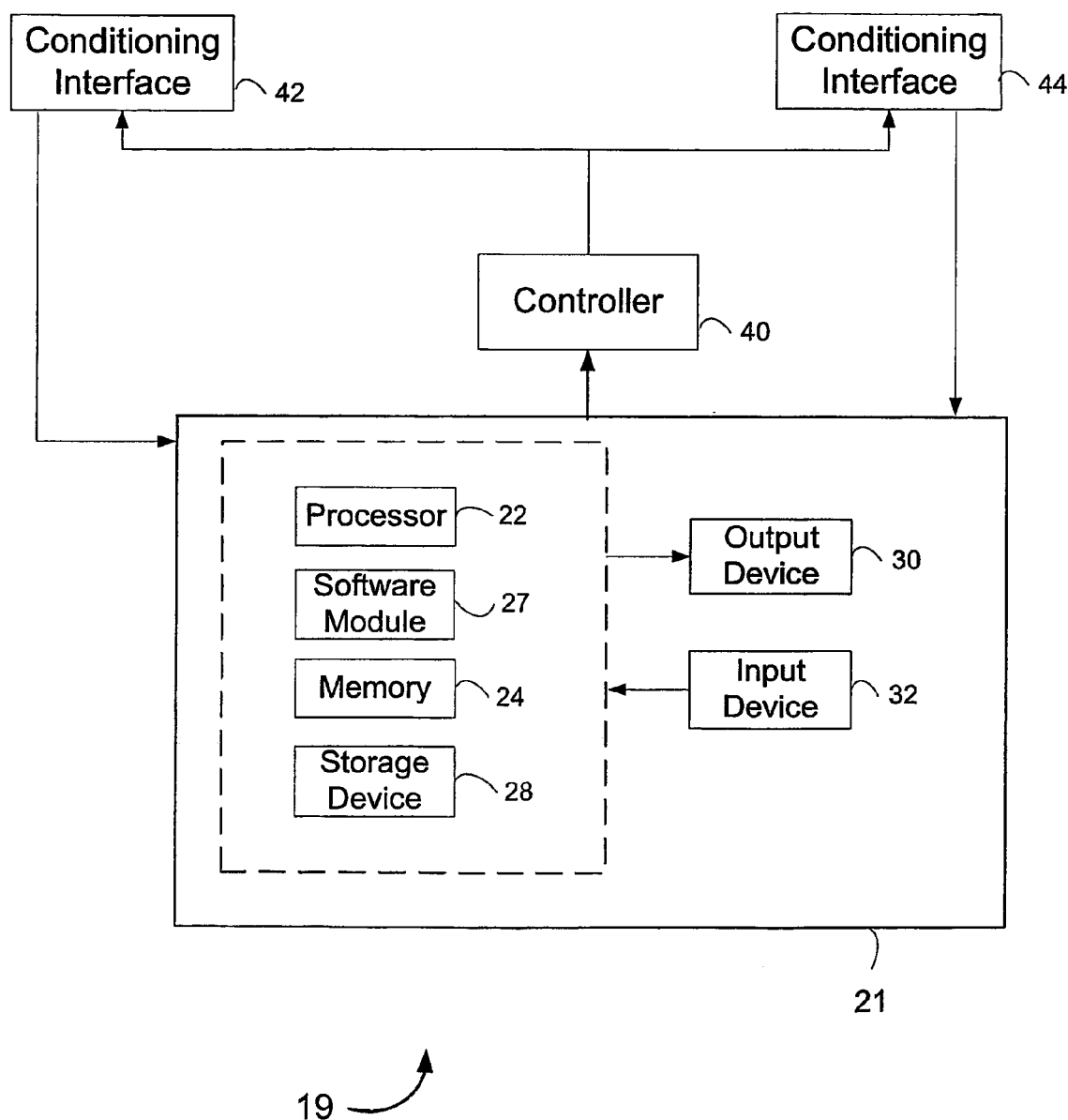
FIG. 1 is a simplified diagrammatic view of a system for the detection of false statements.

With reference to the figures, FIG. 1 shows the components of a system 19 for detection of false statements. In one embodiment, the system 19 is implemented using a computing system 21 such as a programmed general purpose computer which desirably includes a processor 22, memory 24, a storage device 28 such as hard drive, tape drive, or floppy disk, and a software module 27 stored on the storage device 28. In such an embodiment, the system 19 would also include one or more output devices 30 such as a monitor or printer, and one or more input devices 32 such as, for example, a keyboard, mouse, touch display or voice control.

The processor 22 is programmed to operate by the software module 27. The term "module" referenced in this disclosure is meant to broadly cover various types of software code including routines, functions, objects, libraries, classes, members, packages, procedures, methods, or lines of code together performing similar functionality to these types of coding.

In another embodiment, the computing system 21 may be an integrated device such as a laptop computer, tablet PC, or handheld device such as a personal digital assistant. In such an embodiment, one or more the components mentioned above may be built into the computing system 21. It is also envisioned that the present system 19 can be embodied on an internet based system for use by multiple users simultaneously and remote storage and retrieval of information.

Figure 2:
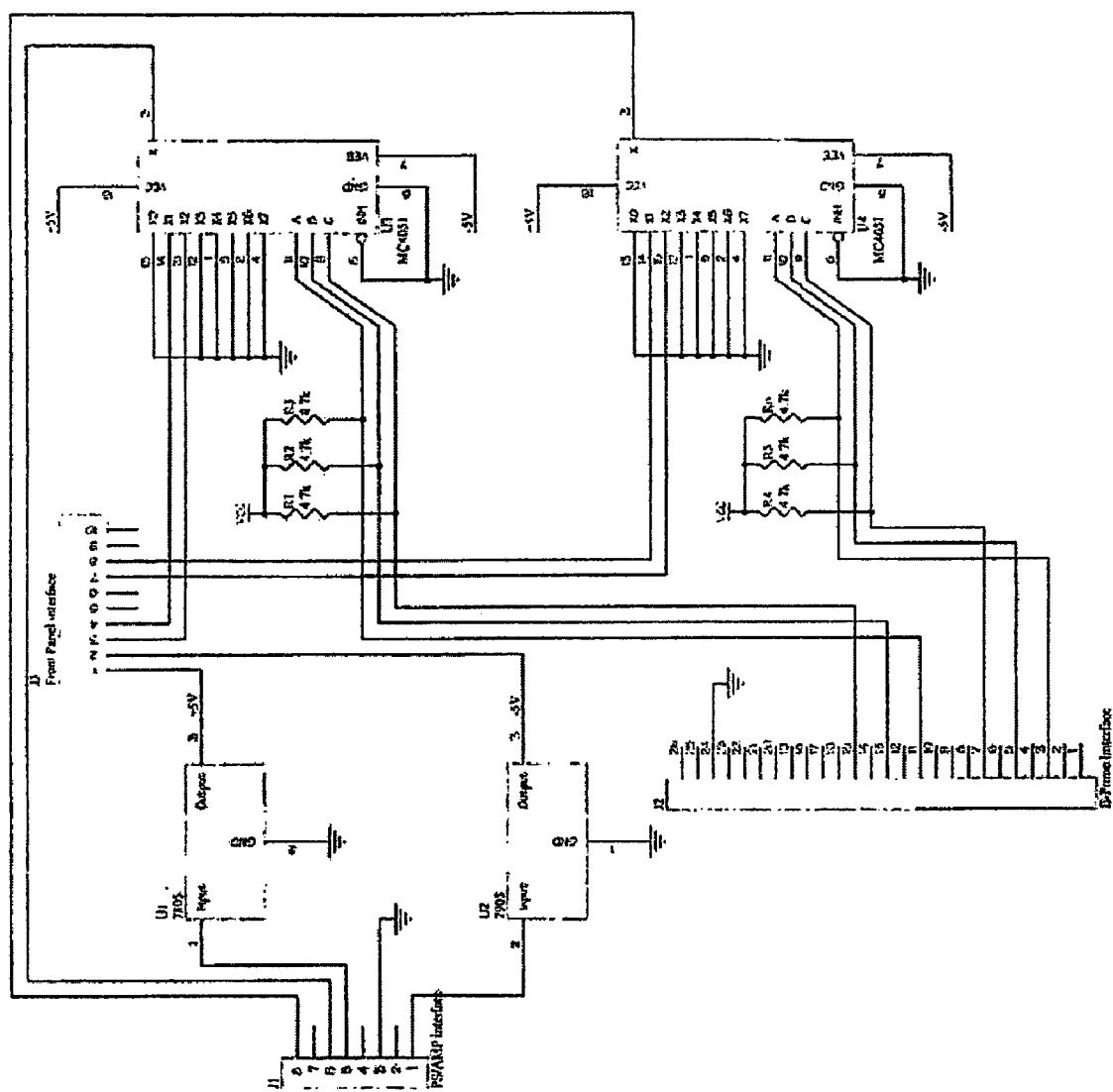
FIG. 2 is a circuit schematic of a first portion of a circuit that controls the application of stimuli to a subject being tested.
Figure 3:
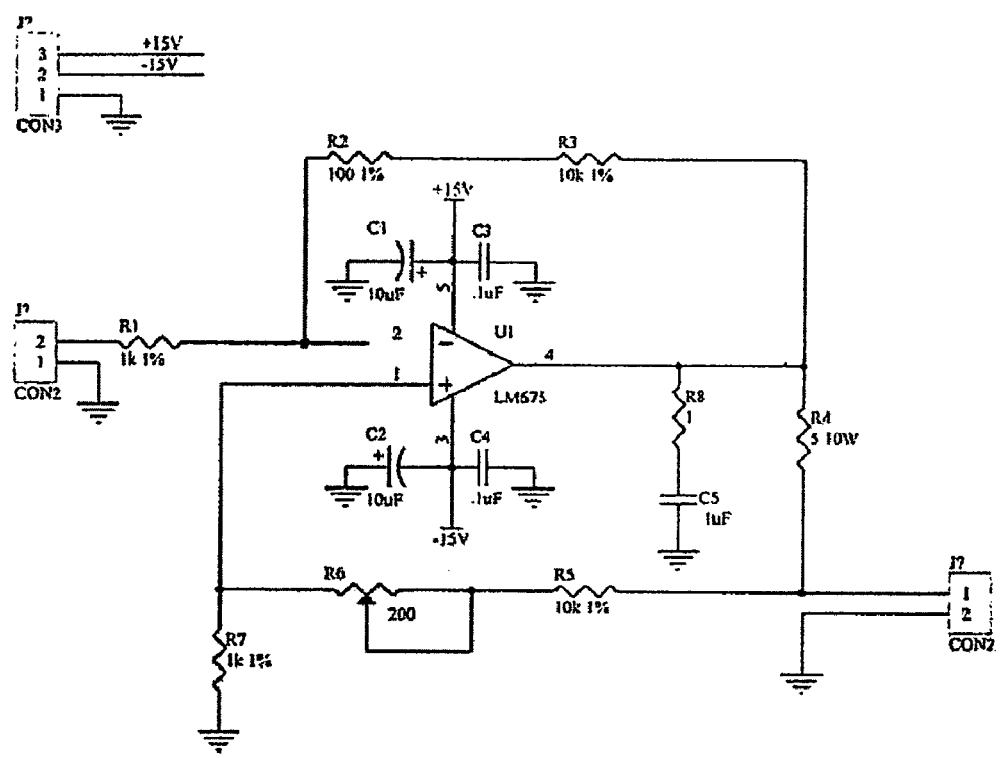
FIG. 3 is a circuit schematic of a second portion of a circuit that controls the application of stimuli to a subject being tested.

The system 19 also includes a controller 40 for operating two or more conditioning interfaces 42, 44. The controller 40 is controlled by the computing system 21. Circuit schematics of portions of one embodiment of controller 40 are shown in FIGS. 2 and 3. The circuit components shown in FIGS. 2 and 3 are common components available from any number of suppliers and therefore are not described in detail for the sake of brevity.

The conditioning interfaces 42, 44 includes an industry standard thermoelectric cooler ("TEC") such as the TEC available from Marlow Industries. The TEC cools when electric current is passed in one direction and heats when the current flow is reversed. The direction and amount of current passing through the TEC is controlled by the controller 40. The TEC is attached to an attachment structure for attachment to a selected body part of a human test subject. The attachment structure may take various forms depending on the selected body part including a clip for attachment to an ear or a strap for attachment to a wrist, hand, arm, or leg.

The conditioning interface 42, 44 is also fitted with a physiological measuring device ("PMD"); such as a plethysmograph, for measuring blood flow at the selected body part. A plethysmograph is an instrument that measures variations in the size of an organ or body part on the basis of the amount of blood passing through or present in the part. In one embodiment, a photoplehtysmograph may be utilized. Other physiological measuring devices, such as devices to record eye blinking, may also be utilized.

Figure 4:
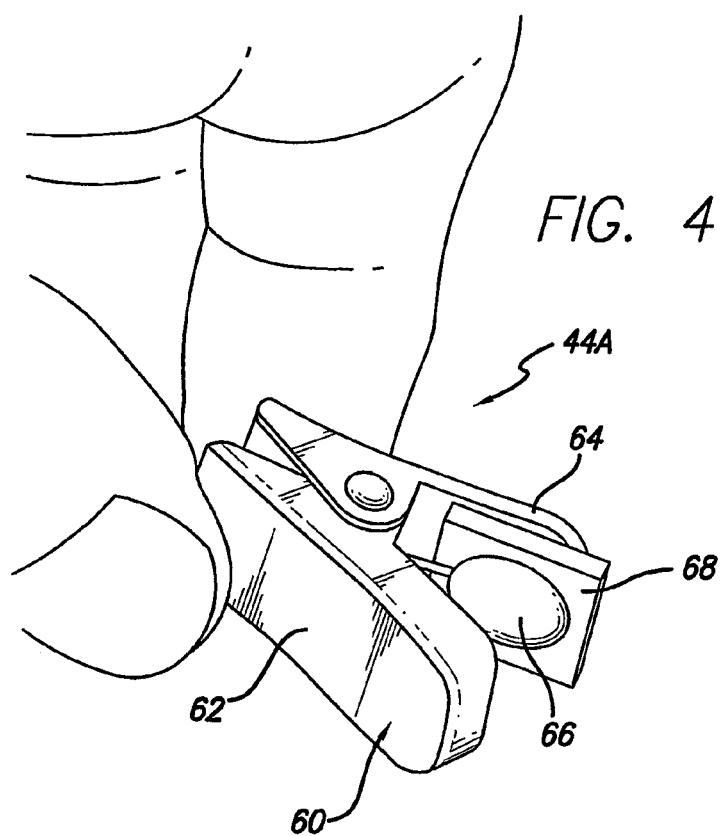
FIG. 4 is a prospective view of one embodiment of a conditioning interface with a clip attachment structure.
Figure 5:
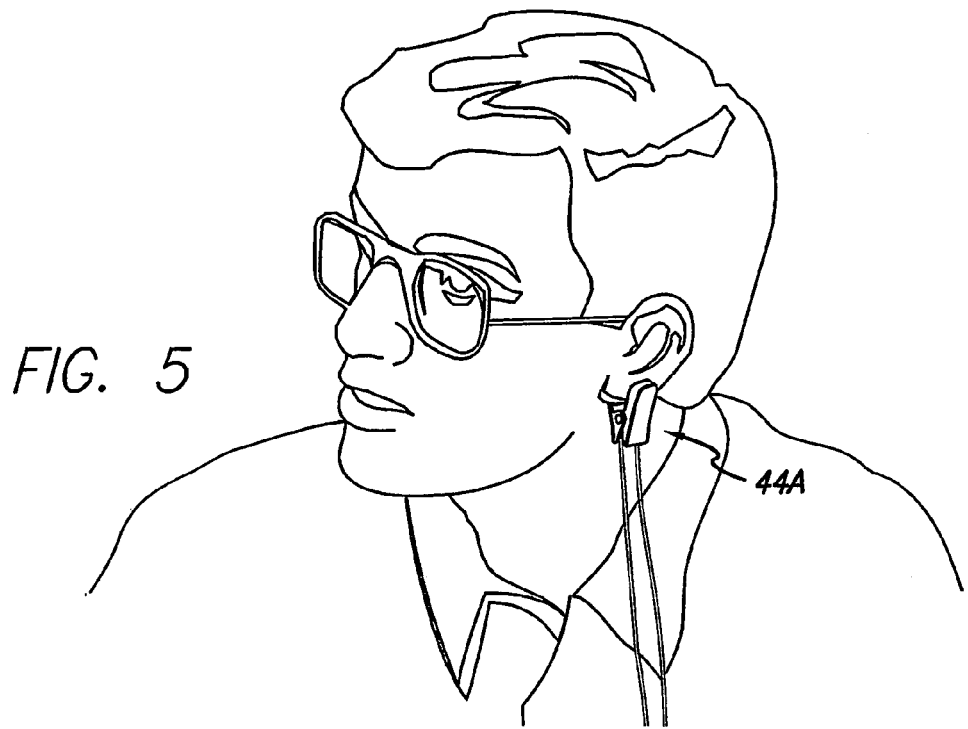
FIG. 5 is the conditioning interface of FIG. 4 shown attached to a subject's ear.

Referring now to FIG. 4, an embodiment of the conditioning interface 44A uses a clip attachment structure 60. Coupled between the arms 62, 64 of the clip 60 is the PMD 66 positioned adjacent to a TEC 68. FIG. 5 shows conditioning interface 44A attached to a subject's ear.

Figure 6:
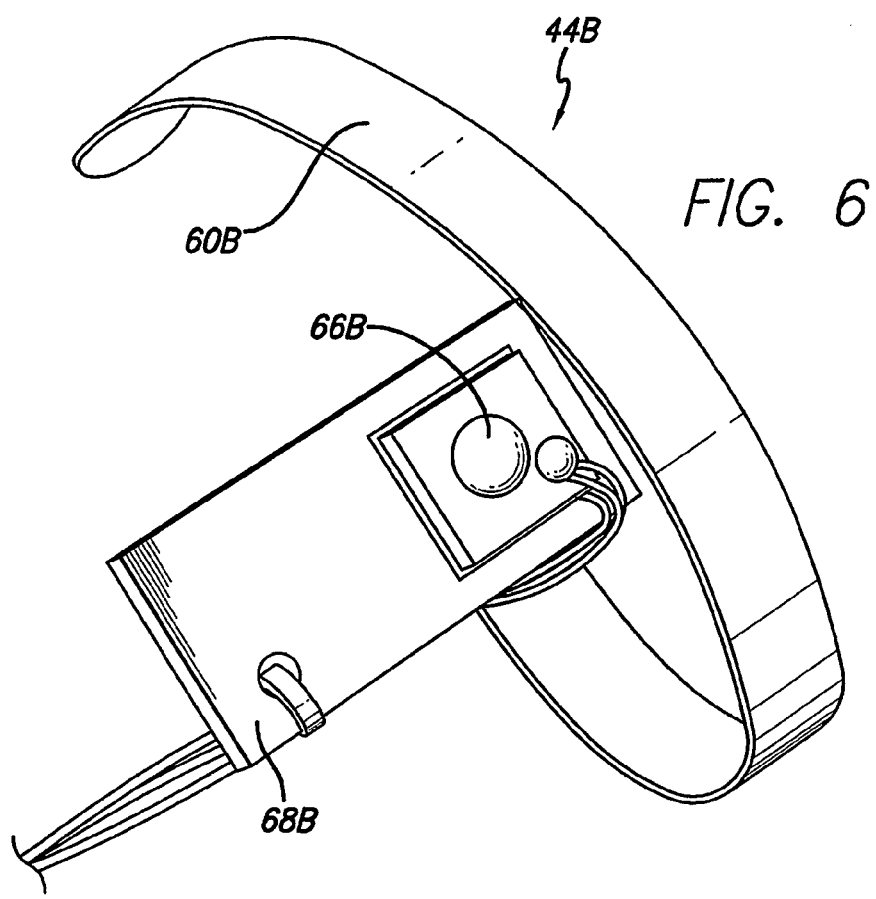
FIG. 6 is a prospective view of another embodiment of a conditioning interface with a strap attachment structure.
Figure 7:
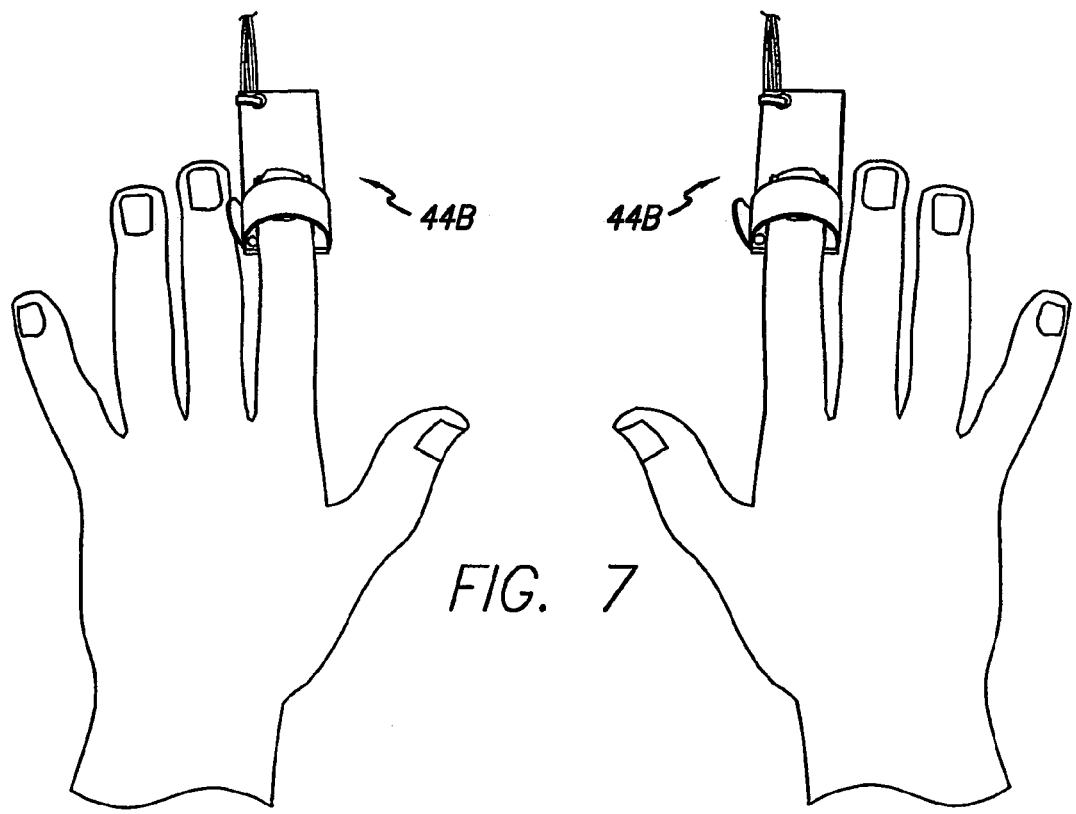
FIG. 7 shows two conditioning interfaces of FIG. 6 attached to a subject's right and left index fingers.

In another embodiment as shown in FIG. 6, a conditioning interface 44B uses a strap attachment structure 60B. A PMD 66B is positioned generally coplanar to the strap 60B when engaged with a body part, such as the tip of an index finger as shown in FIG. 7.

In use, the conditioning interfaces 42, 44 are attached to selected body parts of a test subject. The computing system 21 controls the controller 40 which sends a desired amount and direction of current to each conditioning interface 42, 44. The TEC located within each conditioning interface 42, 44 heats or cools the subject's skin which results in vasoconstriction or vasodilation of the capillaries in that region. This locally alters blood flow. The PMDs provide blood flow data which is sent back to the computing system 21 for storage and analysis.

In an embodiment using a plethysmograph as the PMD, data is collected using photoplethysmographic method. Photoplethysmography produces a relative measure of the amount of blood perfusing the underlying tissue based on the amount of light emitted from an LED that is reflected back and measured by a photoelectric cell. The greater the perfusion of the underlying tissue, the greater the absorption of the emitted light and the less the refracted light to be detected at the photoelectric cell. The units of measurement in photoplethysmography are arbitrary. Although these measures are generally stable at a recording site within a session, they can vary dramatically across sites or whenever a sensor is repositioned. Therefore, the amplitude functions ($f(x_i)$) constituting the time series within a recording site can be expressed as a Z-score, where $Z=[f(x_i)-\text{Mean}(f(x_i))]/\text{Standard Deviation}$. This operation produces time series across recording sites that are on equivalent scales. That is, they are normalized to a mean of zero and a standard deviation of one. The time series from the selected recording sites can be subtracted from one another to produce a different (or composite) waveform useful in the analyzing stage.

The system 19 is operated using the following method. This method may be generally divided into three stages. In a first stage, hereinafter referred to as "training stage", a subject is conditioned to produce a pattern of involuntary responses whenever a true statement is displayed to the subject and to produce a reverse pattern of involuntary responses whenever a false statement is displayed. The second stage, hereinafter called the "testing stage," is to display statements to the subject, the answers to some of which are known to the examiner (control statements) and the answers to which some are not known (test statements). The third stage, hereinafter referred to as an "analyzing stage" involves analyzing data collected during the testing stage to verify differential conditioned responses to (known) true and false statements throughout the testing phase, and assess the truth or falsehood of (intermittent) test statements based on the similarity of the observed pattern of conditioned responses to those associated with known true and false statements.

Preliminarily, the conditioning interfaces 42, 44 are attached to two body parts of the test subject. Although this embodiment of the method utilizes two body parts, it is envisioned that additional conditioning interfaces may be used as well. In one embodiment, the selected body parts are on opposite sides of the body. The selected bodyparts maybe the same on both sides of the subject's body, for example, the left and right index finger, or maybe different body parts on opposite side's of the subject's body, such as the left index finger and the right arm. In another embodiment, the body parts may be on the same side of the body. In another embodiment, one conditioning interface may configured to affect two closely spaced body parts, for example adjacent parts of a hand, arm, or leg. The subject is positioned to communicate with the system 19 using the input device 32 and output device 30. For simplicity, the further description below describes the subject viewing output using a computer screen.

In the first stage, the subject views a series of statements on the computer screen. Each statement has two parts, the first part being displayed for a sufficient time for the user to the read first part of the statement. The screen then clears, and the second statement is displayed, again for a sufficient time for the subject to read and consider the second part of the statement. For example, a displayed first part of a statement may be "I don't like being . . . " followed by a displayed second part of a statement being "honored". Another example may be "I support" as a displayed first part of a statement, followed by the word "terrorism" as a displayed second part of a statement. Optionally, to assure that subjects are paying attention, four seconds after the word completing the sentence appears, a subject may be instructed to input into the system 19 using the input device 32, whether the completion was true or false. In the alternative, the subject may tell a person supervising the method (the "supervisor"), whether the completion was true or false. The instructions to give such a response may be in the form of displayed instructions on the computer screen, or may be given the supervisor. Display of the statement parts is repeated until a pre-programmed number of statements has been displayed or until the supervisor concludes the testing phase.

During the presentation of the sentence completion, but prior to the verbal or inputted response (conditioned stimuli—CS), the system 19 applies temperature stimulation using the conditioning interfaces 42, 44 (unconditioned stimuli—UCS). In an embodiment where two body parts are used, one body part is heated while the other is cooled for a physiological response designated as the "true response." For the "false response," the heating and cooling is reversed. This temperature application is performed during less than all of the of the displayed statements, hereinafter referred to as "trials". For example, the temperature application may be performed during only 80% of the trials. This partial reinforcement is used to avoid the problem of extinction or a reduction in responding. Thus, the perceived veracity of the word completion is conditioned to the temperature change, not the verbal response.

Another embodiment of the training stage makes use of a series of statements about objects or events. A first screen is displayed with a factual statement. A second screen is displayed asking about the first statement. The subject is instructed, either verbally by the supervisor or through displayed instructions, to answer all questions "NO." Differential heating and cooling occurs depending upon whether the trial is true or false. For example, the left hand may cooled and the right hand heated for a true response, and the left hand heated and right hand cooled for a false response. In this manner, the autonomic response is trained.

Figure 8:
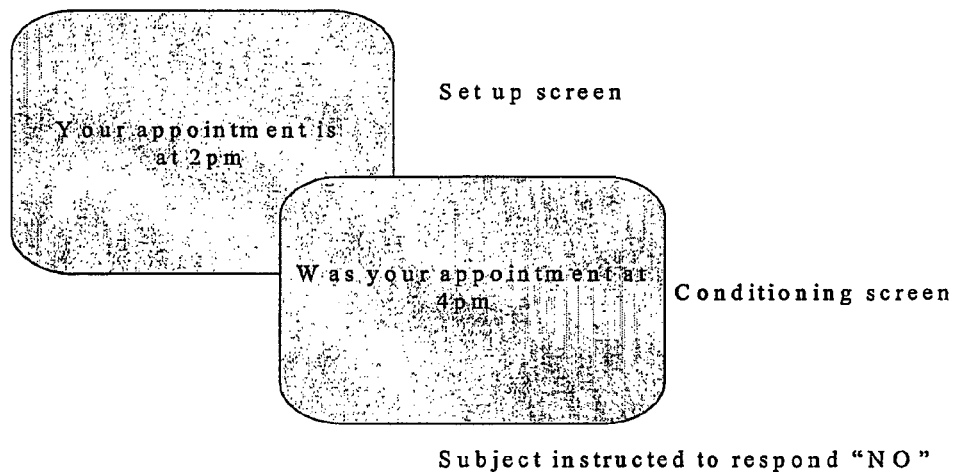
FIG. 8 shows an example of sequential screens used to condition a physiological response.

An example is shown in FIG. 8. In this example, temperature changes are administered when the "4 pm" appears on the screen moments after "Was your appointment at" appears.

In the testing phase, the ratio of temperature-reinforced trials is reduced to 50%. Additionally, true and false sentence completions are added that had not been previously introduced to assess the effect of the conditioning trials on novel stimuli. Approximately forty trials are presented in each phase, although this number can increase or decrease depending on the number of test questions to be examined. Vasomotor response data is continuously recorded from the plethysmographs in the conditioning interfaces 42, 44 (unconditioned and conditioned responses—UR and CR) and sent to the computing device 21 for analysis. The UCS follows less than 100% of the control statements and 0% of the test statements, and each of these statements is presented multiple times to allow ensemble averaging to minimize spontaneous physiological noise.

In the analysis stage, the collected data may be processed to improve confidence in the readings, through statistical methods such as ensemble averaging, normalizing, and filtering. Where two body parts are used, the responses from the first body part are subtracted from the second body part to reduce the oscillatory activity due to cardiac output and differential signal sensitivity across recording sites.

During data collection, the signal from each recording site may be filtered using a filtering device, such as a second order Butterworth band-pass filter, with a pass band of appropriate range, such as between 0.05 and 0.4 Hz. Following the filtering, non-trial data periods were removed and the time series representing photoplethysmographic activity during each trial at each recording site are centered by subtracting the mean value from the time series. This results in a time series of n-measurements at each recording site for each trial.

Although a variety of analysis methods maybe used, one analysis method uses the collected data to produce a composite wave form. The composite waveform is then re-centered by taking the mean of the two seconds preceding the stimulus presentation and subtracting it from the entire composite waveform on a trial by trial basis. Next, composite waveforms (or the component individual time series within site if that is the measure of interest) within each condition (e.g., the UCR trials, trials on which the known answer is true, trials on which the known answer is false, trials in which a specific critical question was asked) from each site are then ensemble averaged. Specifically, a time series of n-measurements on m-trials produce a matrix of m*n size. The ensemble averaged time series is achieved by taking the mean of the measurement at each time point in the time series, resulting in the reduction of the m*n matrix to an n-vector or mean time series for that condition and site. Ensemble averages are produced for all conditions. This processing methodology minimizes noise, particularly the noise due to cardiac activity that produces an oscillatory signal that is relatively similar and time-synched between the two fingers and thus raised the signal to noise ratio of the data substantially.

The computing system 21 is used to calculate ensemble averages for each known control question, with the number of trials ensemble averaged being constant across all control questions and test questions, and may be used to perform the calculations above for analyzing the waveforms.

The conditioning and testing stages are typically performed in the same session. The method has another advantage in that the conditioning stays with the subject for an extended period of time after the session, allowing for further subsequent examination without having to repeat the conditioning procedures.

The computing system 21 compares vasodilatation/constriction associated with known false sentence completions versus the vasoconstriction/dilation associated with known true sentence completions, and distributions of response patterns are specified within subjects. These distributions are then used to evaluate the fit between each and the ensemble averaged conditioned vasomotor patterns observed in response to test questions. Optionally these data may be used to produce receiver operating curves (ROCs) based on observed responses to training questions. Using known signal detection theory, ROCs may then be used to optimize and evaluate the classification of truths and false statements.

Figure 9:
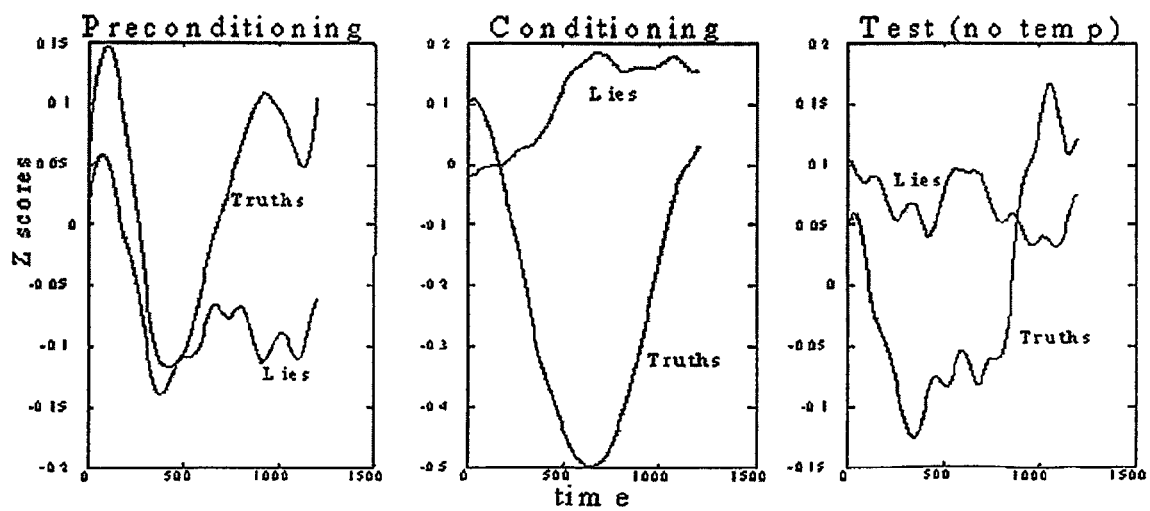
FIG. 9 shows comparative charts of conditioned versus observed physiological responses.

The computer system 21 may be fitted with a communications port for receiving data from the conditioning interfaces 42, 44. In one embodiment, data so received may be stored and imported into a software module specifically written to perform data analysis. An example of software code for receiving the data is shown below in Example 2. In another embodiment, the data may be imported into a spreadsheet, such, as Excel from Microsoft, for manipulation, comparison, and reductive analysis. This filtered data may be plotted in a chart form for easy visual comparison. The program module 27 operates the processor to perform these calculations to allow comparison of the normalized observed patterns with the patterns instilled during the conditioning phase. Where the observed pattern matches the instilled pattern for a false response, the subject is giving false statements. An example of printout comparing the conditioned versus observed results is shown in FIG. 9.

EXAMPLE 1

Differentiation of True and False Statements using Semantic Conditioning Experiment Twelve male college students served as subjects. Following obtaining informed consent and the completion of several questionnaires, two conditioning interfaces were attached to the left and right index fingers of the subjects using hook and loop fasteners. These conditioning interfaces consisted of photoplethysmographs integrated into thermoelectric cooling devices. These devices and their computer interface allowed control of the heating and cooling of the fingers during the presentation of text information on a computer screen.

The conditioning procedures were presented in two phases. The first phase required that subjects view a series of statements on the computer screen. The statements were presented in two parts such as "I don't like being" followed by the word "honored" and "I support" followed by the word "terrorism." To assure that subjects were paying attention, four seconds after the word completing the sentence appeared, subjects were instructed to say if the completion was true or false. During the presentation of the sentence completion but prior to the verbal response (conditioned stimuli—CS), temperature stimulation (unconditioned stimuli—UCS) was applied on 80% of the trials. Thus, the perceived veracity of the word completion was conditioned to the temperature change, not the verbal response. In the second phase, the ratio of temperature reinforced trials was reduced to 50%. Additionally, true and false sentence completions were added that had not been previously introduced to assess the effect of the conditioning trials on novel stimuli. Forty trials were presented in each phase. Vasomotor responses were continuously recorded from the two plethysmographs (unconditioned and conditioned responses—UR and CR) and the record was marked by the computer administering the textual stimuli to indicate the presentation of a completion and whether it was true or false.

The signals from the plethysmographs were normalized, filtered, and the responses from the right finger were subtracted from the left finger. Such processing reduced the oscillatory activity due to cardiac output and potentiated the differences between the two fingers providing for the clear comparison of vasodilatation/constriction associated with false sentence completions versus the vasoconstriction/dilation associated with true sentence completions. Plethysmograph responses of the 12 subjects during the training trials where temperature inductions were associated with true and false statements (CS/UCS pairings) were plotted and averaged. Statistical comparison of these waves indicated that they differed significantly from each other (p=0.01).

EXAMPLE 2

Software Code for Receiving and Analyzing Data from Conditioning Interfaces—Four Modules A. Module 1—"pddVNewOddE.m" is a MATLAB R12 script to analyze data from conditioning and test series. This script provides the following functionality: (1) filters the total record waveforms for the first and second body part; (2) centers the data by subtracting the mean of the whole record; (3) equates the amplitudes of each channel by multiplying each channel by the inverse mean of the absolute value of that channel data; and (4) converts the record into z-scores. Data is recorded into individual trials, maintaining data from left and right channels and adding a difference channel that is the result of subtracting the left and right channels. A baseline correction maybe applied to the subtracted data channel.

Next, the script performs a separation of the epoched trials into sets by their trial type, as determined by the trigger channel data that has been maintained from the beginning of the data processing. The mean subtracted wave from for each trial type is then calculated. The data is then plotted with a option to save the data in MATLAB or ASCII format. Specific variable names such as "Right finger" and "Left finger" are used for illustrative purposes only, as other body parts may be used:

chan2.

%flags

FilterWaves=1; % 0 = no 1 = yes ; flag to Filter Waveforms

EquateAmps=1; % O = no 1 = yes ; flag to Equate Amplitudes

CenterWaves=1; % 0 = No 1 = yes ; flag to center waveforms (NOTE: This must be done to z-score)

ZScore=0; % O = no 1 = yes ; flag to Z-score Data (NOTE: if this is selected, then CenterWaves will be set to 1 as well)

saveafter=1; % O = no 1 = yes ; flag to save selected workspace variables when finished.

SaveAscii=0; % 0 = no 1 = yes ; flag to save all trial types as SaveAscii text files.

wholetrial=1; % O = no 1 = yes ; flag to display whole trial in plot instead of trial from UCS onset only PlotIt=0; % O = no 1 = yes ; flag to plot data at end of function CenterTrials=1;

if (ZScore)

CenterWaves=1;

end

%vars sr=200; %sampling rate z=8; %number of standard deviations for rejection stimdur=2; %stimulus duration trigchan=14; %trigger channel condchan=15; %condition channel leftpulse=4;

rightpulse=5;

locut=.05; %low cut off freq hicut=.4; %hi cut off freq basestart=-2; %when to begin baseline(from stim onset)

windur=8; %window duration in sec respstart=400; %window for physiological response maximum

```
respend=800;
win1=600;     %start of window of interest
win2=1200;    %end of window of interest
removeback=1;  %number of seconds to remove from end of file due to artifact
removefront=1; %number of seconds to remove from front of file due to artifact
prelie=135;    %trial type for preconditioning trials
pretrue=137;
artifact=0;
liestim=[3];   %trial types for UCS lies
truestim=[5];  %trial types for UCS true statements
lies=[107];    %trial code for conditioned lies
truths=[103];  %trial codes for conditioned truths
OutputFileName='-';
% get the file and set the parameters
InFile=strcat(filename,'.txt');
disp(strcat('Loading---',InFile))
a=load(InFile);
[pts chn]=size(a);
data=a(removefront*sr:pts-(removeback*sr),:)'; %remove front and back seconds and transpose
[chan points]=size(data);
disp('Loading complete')
basestart=-1*basestart*sr;
windur=windur*sr;
%digital filter (spectra) here
if(FilterWaves)
  OutputFileName = strcat(OutputFileName,'F');
  data(leftpulse,:)=bandpass(data(leftpulse,:),locut,hicut);
  data(rightpulse,:)=bandpass(data(rightpulse,:),locut,hicut);
end
%%%%%%%remove non-trial intervals
[mark]=find(diff(data(trigchan,:))>0); %find stim onset
```

B. MODULE 2—"PLOTPAIRS" is a function called by MeanByType.m to plot the mean waveforms, on a subject-by-subject basis, for each trial type, plotting the two conditions on the same axes, and the two conditioning/training conditions on another set of axes:

```
function [temp] = MeanByType(Lies,Truths,SaveFlag,Type,UseTypeFlag)
CenterWaves = 0;
set(0,'DefaultAxesLineStyleOrder','-|-.|--|:');
if nargin == 2
    Type = '';
    SaveFlag = 0;
    UseTypeFlag = 0;
end
if nargin == 3
    Type = '';
    UseTypeFlag = 0;
end
if nargin == 4
    UseTypeFlag = 1;
end
if UseTypeFlag == 0
    Type = '';
end
%center
if (CenterWaves)
    [Sbjs, temp] = size(lies);
    for i = 1:Sbjs
        Lies(i,:)=Lies(i,:)-mean(Lies(i,1:600)); %center
        Truths(i,:)=Truths(i,:)-mean(Truths(i,1:600));
    end
end
MinVal=min(min([Lies; Truths]));
MaxVal=max(max([Lies; Truths]));
MaxSize=max(max([size(Lies) size(Truths)]));
V=[ ];
[TruthSize, temp] = size(Truths);
[LieSize, temp] = size(Lies);
fa1 = figure('name',strcat('PlotBySbj:',Type,'1'));
title(strcat('PlotBySbj:',Type,'1'));
SaveName=strcat('PlotBySbj_',Type,'1');
for i=1:(TruthSize/2)
    subplot(2,TruthSize/4,i);
```

-continued

```
%   plot([Lies(i,:);Truths(i,:)]');
    plot(Lies(i,:),'k:');
    hold on
    plot(Truths(i,:),'b');
    hold off
    axis([0 MaxSize MinVal MaxVal]);
    title(strcat('SBJ:',int2str(i),':',Type))
    xlabel(strcat('Samples (',int2str(200),'/second)'))
    ylabel('PPG Output (volts)')
    hold on
    plot([600 600], [MinVal MaxVal],'r-.')
    hold off
    a=i;
end
saveas(fa1,strcat(SaveName,'.fig'))
saveas(fa1,strcat(SaveName,'.jpg'))
fa2 = figure('name',strcat('PlotBySbj:',Type,'2'));
title(strcat('PlotBySbj:',Type,'2'));
SaveName=strcat('PlotBySbj_',Type,'2');
for i=1:(TruthSize/2)
    subplot(2,TruthSize/4,i);
%   plot([Lies(i+a,:);Truths(i+a,:)]');
    plot(Lies(i+a,:),'k:');
    hold on
    plot(Truths(i+a,:),'b');
    axis([0 MaxSize MinVal MaxVal]);
    title(strcat('SBJ:', int2str(a+i),':',Type))
    xlabel(strcat('Samples (',int2str(200),'/second)'))
    ylabel('PPG Output (volts)')
    hold on
    plot ([600 600], [MinVal MaxVal],'r-.')
    hold off
end
saveas(fa2,strcat(SaveName,'.fig'))
saveas(fa2,strcat(SaveName,'.jpg'))
```

C. MODULE 3—"MeanbyType" is a function that takes the data file output by pddVNewOddE.m and calculates the ensemble means for a set of subjects:

```
function [temp] = MeanByType(SubjIds,DVs)
%should PlotPairs be told to print the type info?
UseTypeFlag = 0;
%Should the waveforms be
CenterWaves = 0;
%set defaul for DataVars
DataVars = 'FCEqW'
if nargin == 2
    DataVars=DVs;
end
DVString = DataVars;
DataVars = strcat('-',DataVars);
FileStart = 'VAR9SBJ_';
FileEnd = strcat(DataVars,'.Ensemble.mat');
disp(SubjIds)
[nsubj tmp]=size(SubjIds);
sr = 200;
%Diff_MeanLies = [ ];
%Diff_MeanTruths = [ ];
%Diff_MeanStimLies = [ ];
%Diff_MeanStimTruths = [ ];
L_MeanLies = [ ];
L_MeanTruths = [ ];
L_MeanStimLies = [ ];
L_MeanStimTruths = [ ];
R_MeanLies = [ ];
R_MeanTruths = [ ];
R_MeanStimLies = [ ];
R_MeanStimTruths = [ ];
```

-continued

```
    BaseStarts=[ ];
    WinDurs=[ ];
    for i=1:nsubj
        s = load(strcat(FileStart,num2str(SubjIds(i,:)),FileEnd));
        Diff_MeanLies(i,:) = s.M_Diff_BFNS';
        Diff_MeanTruths(i,:) = s.M_Diff_BTNS';
        Diff_MeanStimLies(i,:) = s.M_Diff_BFS';
        Diff_MeanStimTruths(i,:) = s.M_Diff_BTS';
        L_MeanLies(i,:) = s.Mean_Left_FalseNoUCS';
        L_MeanTruths(i,:) = s.Mean_Left_TrueNoUCS';
        L_MeanStimLies(i,:) = s.Mean_Left_FalseUCS';
        L_MeanStimTruths(i,:) = s.Mean_Left_TrueUCS';
        R_MeanLies(i,:) = s.Mean_Right_FalseNoUCS';
        R_MeanTruths(i,:) = s.Mean_Right_TrueNoUCS';
        R_MeanStimLies(i,:) = s.Mean_Right_FalseUCS';
        R_MeanStimTruths(i,:) = s.Mean_Right_TrueUCS';
        BaseStarts(i,:)=s.basestart';
        WinDurs(i,:)=s.windur';
        clear s
    end
    %center
    if (CenterWaves)
        for i = 1:nsubj
            Diff_MeanLies(i,:) = Diff_MeanLies(i,:)-mean(Diff_MeanLies(i,1:400));
            Diff_MeanTruths(i,:)         =Diff_MeanTruths(i,:)-
mean(Diff_MeanTruths(i,1:400));
            Diff_MeanStimLies(i,:)         =Diff_MeanStimLies(i,:)-
mean(Diff_MeanStimLies(i,1:400));
            Diff_MeanStimTruths(i,:)=Diff_MeanStimTruths(i,:)-
mean(Diff_MeanStimTruths(i,1:400));
            L_MeanLies(i,:) = L_MeanLies(i,:)-mean(L_MeanLies(i,1:400));
            L_MeanTruths(i,:) =L_MeanTruths(i,:)-mean(L_MeanTruths(i,1:400));
            L_MeanStimLies(i,:)         =L_MeanStimLies(i,:)-
mean(L_MeanStimLies(i,1:400));
            L_MeanStimTruths(i,:)=L_MeanStimTruths(i,:)-
mean(L_MeanStimTruths(i,1:400));
            R_MeanLies(i,:) = R_MeanLies(i,:)-mean(R_MeanLies(i,1:400));
            R_MeanTruths(i,:) =R_MeanTruths(i,:)-mean(R_MeanTruths(i,1:400));
            R_MeanStimLies(i,:)         =R_MeanStimLies(i,:)-
mean(R_MeanStimLies(i,1:400));
            R_MeanStimTruths(i,:)=R_MeanStimTruths(i,:)-
mean(R_MeanStimTruths(i,1:400));
        end
    end
    save(strcat('MeanByType',DataVars,'.mat'),'BaseStarts','WinDurs','R_*','Diff_*','L
_*');
    MeanWinDur=mean(WinDurs);
    MeanBaseStart=mean(BaseStarts);
    f1 = figure ('name',strcat(DataVars,' - Grand Means'));
    title(strcat('PDD_NEW_ODD',DataVars, 'Grand Means'));
    MinVal=min(min([mean(Diff_MeanLies);     mean(Diff_MeanTruths);
mean(Diff_MeanStimLies); mean(Diff_MeanStimTruths)]));
    MaxVal=max(max([mean(Diff_MeanLies);     mean(Diff_MeanTruths);
mean(Diff_MeanStimLies); mean(Diff_MeanStimTruths)]));
    MaxSize=max(max([size(Diff_MeanLies)     size(Diff_MeanTruths)
size(Diff_MeanStimLies) size(Diff_MeanStimTruths)]));
    AxisToSet=[0 MaxSize MinVal MaxVal];
    subplot(1,2,2)
    hold on
    ys=[mean(Diff_MeanLies(:,:)); mean(Diff_MeanTruths(:,:))];
    %To plot vertical line at the onset of the stem completion, not the UCS
    VPlotStart = MeanBaseStart + 200
    disp('size(ys)=')
    disp(size(ys))
    %plot(ys))
    %plot([mean(Diff_MeanLies(:,:));mean(Diff_MeanTruths(:,:))]');
    plot(mean(Diff_MeanLies(:,:)),'k:');
    plot(mean(Diff_MeanTruths(:,:)),'b');
    axis([0 MaxSize MinVal MaxVal]);
    V = axis;
    plot([VPlotStart, VPlotStart], [V(1,3),V(1,4)],'r-.')
    hold off
    title('Mean CR')
    xlabel(strcat('Samples (',int2str(sr),'/second)'))
    ylabel('PPG Output (volts)')
    subplot(1,2,1)
    hold on
    axis([0 MaxSize MinVal MaxVal]);
    %plot([mean(Diff_MeanStimLies(:,:));mean(Diff_MeanStimTruths(:,:))]')
```

-continued

```
    plot(mean(Diff_MeanStimLies(:,:)),'k:');
    plot(mean(Diff_MeanStimTruths(:,:)),'b');
    axis([0 MaxSize MinVal MaxVal]);
    title('Mean UCR')
    xlabel(strcat('Samples (',int2str(sr),'/second)'))
    ylabel('PPG Output (volts)')
    V = axis;
    plot([VPlotStart,VPlotStart], [V(1,3),V(1,4)],'r-.')
    plot([MeanBaseStart,MeanBaseStart], [V(1,3),V(1,4)],'m:')
    hold off
    saveas(f1,strcat('GrandMeans',DataVars,'.jpg'))
    saveas(f1,strcat('GrandMeans',DataVars,'.fig'))
    TYPE = '';
    if UseTypeFlag
        TYPE=strcat('(',DVString,')');
    end
    PlotPairs(Diff_MeanStimLies,Diff_MeanStimTruths,1, strcat(TYPE,'UCR'));
    PlotPairs(Diff_MeanLies,Diff_MeanTruths,1, strcat(TYPE,'CR'));
```

D. MODULE 4—"CalcWindowSums" is a function that takes the data output by MeanByType.m script on a selected time period and calculates the mean for each subjectt, in each condition over that time period:

```
    function y = CalcWindowSums(DataVars,WinStart,WinEnd)
%DataVars = '-FCEqZW'
    if nargin<2
        error('Too few inputs');
    elseif nargin>3
        error('Too many arguments');
    end
        s = load(strcat('MeanByType-',DataVars,'.mat'));
    MeanLies = s.Diff_MeanLies;
    MeanTruths = s.Diff_MeanTruths;
    MeanStimLies = s.Diff_MeanStimLies;
    MeanStimTruths = s.Diff_MeanStimTruths;
    clear s;
    if nargin==3
        SumMeanTruths = sum(MeanTruths(:,WinStart:WinEnd),2);
        SumMeanLies = sum(MeanLies(:,WinStart:WinEnd),2);
        SumMeanStimTruths = sum(MeanStimTruths(:,WinStart:WinEnd),2);
        SumMeanStimLies = sum(MeanStimLies(:,WinStart:WinEnd),2);
        SumUCR(:,1)=SumMeanTruths ;
        SumUCR(:,2)=SumMeanLies ;
        SumUCR(:,3)=SumUCR(:,1)-SumUCR(:,2) ;
        SumCR(:,1)=SumMeanStimTruths ;
        SumCR(:,2)=SumMeanStimLies ;
        SumCR(:,3)=SumCR(:,1)-SumCR(:,2) ;
    elseif nargin==2
        SumMeanTruths = sum(MeanTruths(:,WinStart:end),2);
        SumMeanLies = sum(MeanLies(:,WinStart:end),2);
        SumMeanStimTruths = sum(MeanStimTruths(:,WinStart:end),2);
        SumMeanStimLies = sum(MeanStimLies(:,WinStart:end),2);
        SumUCR(:,1)=SumMeanTruths;
        SumUCR(:,2)=SumMeanLies;
        SumUCR(:,3)=SumUCR(:,1)-SumUCR(:,2);
        SumCR(:,1)=SumMeanStimTruths;
        SumCR(:,2)=SumMeanStimLies;
        SumCR(:,3)=SumCR(:,1)-SumCR(:,2);
    end
    save(strcat('MeanSums-
',DataVars,int2str(WinStart),'to',int2str(WinEnd),'.mat'),'Sum*','Win*');
    save(strcat('SumUCR-',DataVars,int2str(WinStart),'to',
        int2str(WinEnd),'.txt'),
'SumUCR', '-ascii', '-double', '-tabs');
    save(strcat('SumCR-',DataVars,int2str(WinStart),'to',
        int2str(WinEnd),'.txt'),
'SumCR', '-ascii', '-double', '-tabs')
```

While a embodiments of the invention are shown and described, it is envisioned that those skilled in the art may devise various modifications and equivalents without departing from the spirit and scope of the disclosure as recited in the following claims.

Documents Cited

National Research Council. (2002). *The Polygraph and Lie Detection*. Report by the Committee to Review the Scientific Evidence on the Polygraph. Division of Behavioral and Social Sciences and Education. Washington, D.C.: The National Academies Press.

What is claimed is:

1. A system for detecting false statements made by a subject, the system comprising:
   (a) a programmed computing device, the programmed computing device including a software module operative to;
      (i) condition a subject to produce an involuntary physiological response pattern which is not a naturally occurring physiological response, when the subject states a false statement, and an opposite response pattern to a true statement; and to
         A. present the subject with a plurality of questions, the answer to some of which are known in advance;
         B. record the subject's answers to the plurality of questions while contemporaneously recording data related to the involuntary physiological responses; and
      (ii) analyze the recorded data to determine whether the subject is providing false statements by comparing conditioned responses to the statements to the distribution of conditioned responses shown to known true and known false statements;
   (b) an output device configured to receive data from the programmed computing device;
   (c) a controller configured to be operated by the programmed computing device;
   (d) at least one conditioning interface controllably operated by the controller, each conditioning interface further comprising:
      i. an attachment structure for attaching the conditioning interface to a selected body part of the subject; and
      ii. a physiological measurement device.

2. A method of using a system for detecting false statements made by a subject, the system comprising a programmed computing device, an output device, a controller, and at least one controlling conditioning interface, the method comprising the steps of:
(a) attaching at least one conditioning interface to the subject;
(b) conditioning the subject to produce an involuntary physiological response which is not a naturally occurring physiological response pattern when the subject states a false statement, and an opposite response pattern to a true statement;
(c) subjecting the subject to a testing stage comprising the steps of:
 i. presenting the subject with a plurality of questions which are answered by statements, the answers to some of which are known in advance;
 ii. recording the subject's answers to the plurality of questions while contemporaneously recording data related to the involuntary physiological response; and
(d) analyzing the recorded data to determine whether the subject is providing false statements by comparing conditioned responses to the statements, to the distribution of conditioned responses shown to known true and known false statements.

3. The method of claim 2, wherein the step of conditioning the subject to produce an involuntary physiological response is comprised of the following steps:
(a) exposing the subject to a statement that is a true statement to the subject;
(b) stimulating a first body part of the subject with a first stimulus and contemporaneously stimulating a second body part of the subject with a second stimulus to obtain a first physiological response, the first physiological response being designated as a true response;
(c) repeating a cycle of steps a–b.

4. The method of claim 3, comprising a further step between step b and step c, wherein the further step is stimulating the first body part with second stimulus and the second body part with the first stimulus to obtain a second physiological response, the second physiological response designated as a false response.

5. The method of claim 3, wherein exposing the subject to a statement is displaying the statement onscreen.

6. The method of claim 3, wherein exposing the subject to a statement is by producing the statement audibly for the subject to hear.

7. The method of claim 3, wherein the first physiological response is a vasoconstriction of blood vessels in the first body part, and vasodilation of the blood vessels in the second body part.

8. The method of claim 4, wherein the first physiological response is a vasoconstriction of blood vessels in the first body part, and vasodilation of the blood vessels in the second body part and the second physiological response is vasoconstriction of blood vessels in the second body part, and vasodilation of the blood vessels in the first body part.

9. The method of claim 3, wherein the first physiological response is a blinking of an eye.

10. The method of claim 3, wherein the first stimulus and second stimulus is only applied during a subset of the cycle.

11. A method of detecting false statements made by a subject comprising the steps of:
(a) conditioning the subject to produce an involuntary physiological response which is not a naturally occurring physiological response pattern, when the subject provides false statements, and an opposite response pattern to a true statement;
(b) asking the subject to state whether a series of statements presented to the subject are true and monitoring for the involuntary response during the subject's answers; and
(c) detecting whether the subject is providing false statements based on whether the involuntary response associated with a false statement is observed during the subject's answers.

12. The method of claim 11, wherein the step of conditioning the subject to produce an involuntary physiological response is comprised of the following conditioning steps:
(a) exposing the subject to a statement that is a true statement to the subject;
(b) stimulating a first body part of the subject with a first stimulus and contemporaneously stimulating a second body part of the subject with a second stimulus to obtain a first physiological response, the first physiological response being designated as a true response;
(c) repeating a cycle of conditioning steps a–b.

13. The method of claim 12, comprising a further step in the cycle of stimulating the first body part with second stimulus and the second body part with the first stimulus to obtain a second physiological response, the second physiological response designated as a false response.

14. The method of claim 12, wherein exposing the subject to a statement is displaying the statement onscreen.

15. The method of claim 12, wherein exposing the subject to a statement is by producing the statement audibly for the subject to hear.

16. The method of claim 12, wherein the first physiological response is a vasoconstriction of blood vessels in the first body part, and vasodilation of the blood vessels in the second body part.

17. The method of claim 12, wherein the first physiological response is a vasoconstriction of blood vessels in the first body part, and vasodilation of the blood vessels in the second body part and the second physiological response is vasoconstriction of blood vessels in the second body part, and vasodilation of the blood vessels in the first body part.

18. The method of claim 12, wherein the first physiological response is a blinking of an eye.

19. The method of claim 12, wherein the first stimulus and second stimulus is only applied during a subset of the cycle.

* * * * *